United States Patent [19]

Hata et al.

[11] 4,247,569
[45] Jan. 27, 1981

[54] ANTIBACTERIAL AGENTS

[75] Inventors: Kunio Hata, Soka; Motoo Matsukura, Tokyo; Satoshi Hatano, Tokyo; Kihachiro Ohsima, Tokyo; Isao Kano, Tokyo; Hiroaki Umeda, Tokyo; Haruo Awaji, Tokyo, all of Japan

[73] Assignee: Jujo Paper Co., Ltd., Tokyo, Japan

[21] Appl. No.: 81,189

[22] Filed: Oct. 2, 1979

Related U.S. Application Data

[60] Continuation-in-part of Ser. No. 969,532, Dec. 14, 1978, abandoned, which is a division of Ser. No. 893,450, Apr. 4, 1978, abandoned.

[30] Foreign Application Priority Data

Apr. 7, 1977 [JP] Japan ................... 52-39761

[51] Int. Cl.³ .................................. A23L 3/34
[52] U.S. Cl. ................................. 426/335; 426/532
[58] Field of Search ............................ 426/335, 532

[56] References Cited

U.S. PATENT DOCUMENTS

| 3,352,759 | 11/1967 | Hara | 426/335 X |
| 3,510,317 | 5/1970 | Fernholz | 426/335 X |
| 3,623,884 | 11/1971 | Haas | 426/335 X |
| 3,694,224 | 9/1972 | Rubio | 426/335 X |
| 3,899,588 | 8/1975 | Skov | 426/335 X |
| 4,011,346 | 3/1977 | Ernst | 426/335 X |

OTHER PUBLICATIONS

Chem. Abst., vol. 78, No. 78: 122684 g, 1973.

Primary Examiner—Robert A. Yoncoskie
Attorney, Agent, or Firm—Stevens, Davis, Miller & Mosher

[57] ABSTRACT

An antibacterial agent comprising one of dicarboxylic compounds or alkali metal salts thereof generally given by the formula

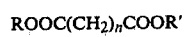

ROOC(CH$_2$)$_n$COOR' wherein R and R' are a hydrogen or an element of the alkali metal group, respectively, and n is an integer ranging from 11 to 14 inclusive, or a mixture of two or more of said compounds or alkali metal salts thereof, said antibacterial agent being stable in an aqueous solution and a small amount of addition thereof to foods exhibiting an improved antibacterial effect on gram-positive bacteria such as *Staphylococcus aureus* and *Bacillus subtilis*.

6 Claims, No Drawings

ANTIBACTERIAL AGENTS

This is a continuation-in-part application of application Ser. No. 969,532, filed Dec. 14, 1978, now abandoned, which in turn is a divisional application of application Ser. No. 893,450, filed Apr. 4, 1978, now abandoned.

The present invention relates to an antibacterial agent comprising one of straight-chain saturated dicarboxylic acids or an alkali metal salts thereof or a mixture of two or more of said dicarboxylic acids or alkali metal salts thereof and it provides such a non-medical antibacterial agent having an improved antibacterial property.

Hetertofore, since the food contamination with bacteria and microorganisms has caused not only a deterioration of taste but also a food putrefaction or poisoning, several kinds of antibacterial agents have been used to improve the preservability of foods.

Therefore, antibacterial agents such as monoglyceride caprate or sodium propionate have been used to prevent the food contamination with bacteria or microorganisms during the course of processing or distribution thereof. However, since such conventional antibacterial agents do not have a sufficient antibacterial ability, it has been proposed to add an acid together therewith for maintaining the pH at a lower level to reinforce the antibacterial ability.

However, the use of such a method according to the prior art as mentioned above has been limited in that it is effective, by its own nature, only to acidic foods because of sourness caused by an acid added thereto. Especially, in the case of monoglyceride caprate, its use is limited from the viewpoint of long-term stability, because an ester bond existing in the molecule thereof renders it readily susceptible to hydrolysis.

Accordingly, an object of the present invention is to provide an antibacterial agent which has an improved antibacterial ability as well as safety and in which the aforementioned shortcomings of the prior art antibacterial agents are eliminated.

The inventors have found that a substance having an antibacterial activity exists in the bark and lignum of Hybrid Aspen ($F_1$ Hybrid of Japanese Aspen; Populus sieboldic MIQ, and Canadian Aspen; Big tooth Aspen Populus grandidentata $MICH_x$) and isolated said substance and identified to be azelaic acid. Then, the inventors have achieved the present invention as a result of a series of intensive studies on the antibacterial activity of straight-chain saturated dicarboxylic acids and metal salts thereof which are analogs of azelaic acid.

As shown in Tables 1, 2 and 3 and mentioned hereafter, the antibacterial agent according to the present invention comprises one of the compounds generally given by the formula

$$ROOC(CH_2)_nCOOR'$$

wherein R and R' are a hydrogen of an element of alkali metal group, respectively, and n is an integer ranging from 11 to 14 inclusive, or a mixture thereof.

In the meantime, those carboxylic acids having a carbon number of 5 or less give a lower pH in the state of an aqueous solution, while those having a carbon number larger than 18 are not suitable for a practical use because of much decreased solubility and weak antibacterial effect. Also, it is preferable to use a sodium salt as the alkali metal salt because it can be produced with the highest purity at a lower cost as compared with potassium salts entailing a higher cost and lower purity.

The antibacterial agent given by the aforementioned formula can be readily obtained by extraction from the bark or lignum of trees of the aforementioned poplar family or by a simple oxidation of a naturally existing material. Also, it is well-known that aliphatic acids such as monocarboxylic acids are subjected to an omega oxidazation to be turned into a dicarboxylic acid by an enzymatic action when taken in a living body and finally excreted as a metabolic excreta after playing a certain physiological role in the living body, and it can be expected that the dicarboxylic acid compounds have an extremely low toxicity. In view of this, the antibacterial agent according to the present invention has advantageous characteristics as a food preservative.

The compounds given by the aforementioned formula has a strong antibacterial ability as mentioned herein before. Especially, the dialkali metal salts having a carbon number of 13 to 16 inclusive have an antibacterial activity on the bacteria such as *Staphylococcus aureus, Bacillus subtilis* or *Escherichia coli* 7 to 80 times stronger than monoglyceride caprate. Therefore, the added quantity of said compounds according to the present invention can be reduced to 1/7 to 1/80 of the conventional antibacterial agents and the handling thereof can be further facilitated.

In application of the antibacterial agent according to the present invention, one of the compounds given by the aforementioned formula or a mixture of two or more of said compounds may be mixed into foods such as bread or soy cake or materials thereof, or may be added thereto in combination with other food additives such as surfactants, without sacrificing the antibacterial effect et al. The addition of about 0.005 to 0.1% (by weight) thereof can exhibit a sufficient effect as a food additive.

Hereinafter, the present invention will be described further in detail by way of preferred embodiments thereof.

PREFERRED EMBODIMENT NO. 1

One loop was inoculated from slant culture of *Staphylococcus aureus* and *Bacillus subtilis*, respectively, into a liquid culture medium containing 1% of glucose, 0.5% of meat juice extract, 0.5% of peptone and 0.3% of sodium chloride and separately subjected to a pre-culture at 37° C. for 24 hours. Then, each 0.1 m of said two resultant cultures from said pre-culture was separately inoculated into 10 m of each of three culture media having the same composition as that used for said pre-culture, to which the antibacterial agent according to the present invention, conventional monoglyceride caprate and sodium propionate were respectively added. Then, these three cultures were subjected to a shake culture in a L-tube at 30° C. for 24 hours. Consequently, the concentration of the antibacterial agents at which the growth of each bacterial could be inhibited was determined on the basis of the turbidity of culture due to the growth of bacteria (absorbance at the wave-length of 660 m was measured by means of a spectrophotometer).

Table 1 shows the relationship between antibacterial agents and the minimum concentration thereof activity to inhibit the growth of bacteria.

TABLE 1

Minimum inhibitory concentrations (mg/l)

| Compounds | Staphylococcus aureus | Bacillus subtilis |
|---|---|---|
| Pimelic acid $HOOC(CH_2)_5COOH$ | 300 | 350 |
| Disodium pimelate | 4000 | 4000 |
| Suberic acid $HOOC(CH_2)_6COOH$ | 200 | 200 |
| Disodium suberate | 3000 | 2500 |
| Azelaic acid $HOOC(CH_2)_7COOH$ | 150 | 150 |
|  | 150 | 150 |
| Disodium azelate | 2000 | 1500 |
| Sebacic acid $HOOC(CH_2)_8COOH$ | 120 | 150 |
| Disodium sebacate | 1200 | 500 |
| 1,9-nonamethylene dicarboxylic acid $HOOC(CH_2)_9COOH$ | 75 | 80 |
| Disodium 1,9-nonamethylene dicarboxylate | 400 | 200 |
| 1,10-decamethylene dicarboxylic acid $HOOC(CH_2)_{10}COOH$ | 30 | 30 |
| Disodium 1,10-decamethylene dicarboxylate | 150 | 75 |
| Brassylic acid $HOOC(CH_2)_{11}COOH$ | 20 | 30 |
| Disodium brassylate | 50 | 35 |
| 1,12-dodecamethylene dicarboxylic acid $HOOC(CH_2)_{12}COOH$ | 10 | 25 |
| Disodium 1,12-dodecamethylene dicarboxylate | 30 | 30 |
| 1,13-tridecamethylene dicarboxylic acid $HOOC(CH_2)_{13}COOH$ | 10 | 10 |
| Disodium 1,13-tridecamethylene dicarboxylate | 30 | 30 |
| 1,14-tetradecamethylene dicarboxylic acid $HOOC(CH_2)_{14}COOH$ | 10 | 15 |
| Disodium 1,14-tetradecamethylene dicarboxylate | 40 | 35 |
| 1,15-pentadecamethylene dicarboxylic acid $HOOC(CH_2)_{15}COOH$ | 30 | 30 |
| Disodium 1,15-pentadecamethylene dicarboxylate | 120 | 100 |
| 1,16-hexadecamethylene dicarboxylic acid $HOOC(CH_2)_{16}COOH$ | 50 | 50 |
| Disodium 1,16-hexadecamethylene dicarboxylate | 300 | 250 |
| 1,17-heptadecamethylene dicarboxylic acid $HOOC(CH_2)_{17}COOH$ | 90 | 110 |
| Disodium 1,17-heptadecamethylene dicarboxylate | 800 | 600 |
| 1,18-octadecamethylene dicarboxylic acid $HOOC(CH_2)_{18}COOH$ | 150 | 150 |
| Disodium 1,18-octadecamethylene dicarboxylate | 2500 | 1500 |
| 1,19-nonadecamethylene dicarboxylic acid $HOOC(CH_2)_{19}COOH$ | 400 | 350 |
| Disodium 1,19-nonadecamethylene dicarboxylate | 4000 | 4000 |
| Prior art Monoglyceride caprate | 500 | 250 |
| Prior art Sodium propionate | 100 | 2500 |

PREFERRED EMBODIMENT NO. 2

A predetermined quantity of each of two bacteria, namely, Staphylococcus aureus and Bacillus subtilis, pre-cultured in the same method as the preferred embodiment No. 1 was inoculated into two different culture media (culture media composition being the same as the pre-culture of the preferred embodiment No. 1) of pH6 and pH7, respectively. Then, in the same method as the preferred embodiment No. 1, the concentration of the antibacterial agents at which the growth of each bacteria could be inhibited was determined to observe the effect of pH level on said minimum concentration. The results are summarized in Table 2.

TABLE 2

Minimum inhibitory concentrations (mg/l)

| Compounds | | pH | Staphylococcus aureus 6 | 7 | Bacillus subtilis 6 | 7 |
|---|---|---|---|---|---|---|
| $(CH_2)_7(COONa)_2$ | | | 2000 | 4000 | 1500 | 5000 |
| $(CH_2)_{11}(COONa)_2$ | | | 75 | 200 | 35 | 300 |
| $(CH_2)_{12}(COONa)_2$ | | | 30 | 150 | 30 | 250 |
| $(CH_2)_{13}(COONa)_2$ | | | 30 | 150 | 30 | 250 |
| Prior art | Sodium propionate | | 500 | 1700 | 250 | 650 |
| | Monoglyceride caprate | | 1000 | 2500 | 2500 | 6000 |

PREFERRED EMBODIMENT NO. 3

A predetermined quantity of each of two bacteria, namely, Staphylococcus aureus and Bacillus subtilis, pre-cultured in the same method as the preferred embodiment No. 1 was inoculated into a culture medium (having the same composition as the preferred embodiment No. 1) of pH6 containing equimolar mixture of the antibacterial agents according to the present invention. Then in the same manner as the preferred embodiment No. 1, minimum concentration at which the growth of bacteria could be inhibited was determined. The results are summarized in Table 3.

TABLE 3

Minimum inhibitory concentrations (mg/l)

| Compounds | Staphylococcus aureus | Bacillus subtilis |
|---|---|---|
| $(CH_2)_7(COOH)_2$ $(CH_2)_{10}(COONa)_2$ | 130 | 100 |
| $(CH_2)_7(COOH)_2$ $(CH_2)_{11}(COOH)_2$ | 70 | 80 |
| $(CH_2)_{12}(COOH)_2$ $(CH_2)_{13}(COONa)_2$ | 25 | 30 |
| Prior art Monoglyceride caprate | 500 | 250 |
| Prior art Sodium propionate | 1000 | 2500 |

PREFERRED EMBODIMENT NO. 4

8 kg of Soybean milk was prepared from soybean 2 kg in the usual way. 0.01% of each antibacterial agent according to the present invention which was dissolved or suspended in water was added to the Soybean milk. This mixture was charged into polyethylene tube and 0.3% of δ-glucuronolactone was added further, which was heated at 90° C. for 40 minutes. Then this preparation (Beans curd) was sealed and kept at 20° C. In order to observe the state of putrefication of each soybean curd, Variable cell count was determined every day. The results are summarized in Table 4.

TABLE 4
PRESERVABLE EFFECT OF SOYBEAN CURD

| Compounds | Variable cell counts (counts/g) Number of Day | | | | | |
|---|---|---|---|---|---|---|
| | 0 | 1 | 2 | 3 | 4 | 5 |
| $(CH_2)_{11}(COOH)_2$ | (—) | (—) | (—) | (—) | (—) | $1.2 \times 10^3$ |
| $(CH_2)_{11}(COONa)_2$ | (—) | (—) | (—) | (—) | $6.7 \times 10^2$ | $8.5 \times 10^3$ |
| $(CH_2)_{12}(COOH)_2$ | (—) | (—) | (—) | (—) | (—) | $4.7 \times 10^3$ |
| $(CH_2)_{12}(COONa)_2$ | (—) | (—) | (—) | (—) | $4.5 \times 10^2$ | $5.0 \times 10^3$ |
| $(CH_2)_{13}(COOH)_2$ | (—) | (—) | (—) | (—) | (—) | $5.2 \times 10^2$ |
| $(CH_2)_{13}(COONa)_2$ | (—) | (—) | (—) | (—) | $4.1 \times 10^2$ | $4.3 \times 10^3$ |
| $(CH_2)_{14}(COOH)_2$ | (—) | (—) | (—) | (—) | (—) | $8.1 \times 10^2$ |
| $(CH_2)_{14}(COONa)_2$ | (—) | (—) | (—) | (—) | $5.5 \times 10^2$ | $7.6 \times 10^3$ |
| Control | (—) | (—) | (—) | $227 \times 10^3$ | $6.1 \times 10^4$ | $4.0 \times 10^5$ |

(—): Variable cell counts is below 300

PREFERRED EMBODIMENT NO. 5

A predetermined quality of each of four microorganisms, namely *Escherichia Coli, Pseudomonas aeruginosa, Penicillium citrinum* and *Candida albicans,* pre-cultured in the same method as the preferred embodiment No. 1 was inoculated into a culture media (having the same composition as the preferred embodiment No. 1) containing the antibacterial agents according to the present invention. Then in the same manner as the preferred embodiment No. 1 minimum concentration at which the growth of microorganisms could be inhibited was determined. The results are summarized in Table 5.

TABLE 5
MINIMUM INHIBITORY CONCENTRATIONS (mg/l)

| Compound of present invention | Microorganisms | | | |
|---|---|---|---|---|
| | Escherichia coli | Pseudomonas aeruinosa | Penicillium citrinum | Candida albicans |
| $(CH_2)_{11}(COOH)_2$ | 1000 | (—) | (—) | (—) |
| $(CH_2)_{12}(COOH)_2$ | 1000 | (—) | (—) | (—) |
| $(CH_2)_{13}(COOH)_2$ | 1500 | (—) | (—) | (—) |
| $(CH_2)_{14}(COOH)_2$ | 2000 | (—) | (—) | (—) |

*(—); No inhibition at 2000 (mg/l)

What is claimed is:

1. A food containing an antibacterial agent of the formula

ROOC(CH$_2$)$_n$COOR' wherein R and R' are hydrogen or an element of the alkali metal group and n is an integer ranging from 11 to 14 inclusive in a quantity of from 0.005 to 0.1% by weight.

2. The food of claim 1 wherein R is an alkali metal selected from the group consisting of sodium and potassium.

3. The food of claim 2 wherein R is sodium.

4. A method for the prevention of bacterial growth in food comprising incorporating into said food from 0.005 to 0.01% by weight of an antibacterial agent of the general formula ROOC(CH$_2$)$_n$COOR' wherein R and R' are hydrogen or an element of the alkali metal group and n is an integer ranging from 11 to 14 inclusive.

5. The method of claim 4 wherein R is an alkali metal selected from the group consisting of sodium and potassium.

6. The method of claim 5 wherein R is sodium.

* * * * *